US005693324A

United States Patent [19]

Edwards

[11] Patent Number: 5,693,324
[45] Date of Patent: Dec. 2, 1997

[54] TRIS(ISONITRILE) COPPER(I) SULFATES FOR PREPARING RADIONUCLIDE COMPLEXES

[75] Inventor: David Scott Edwards, Burlington, Mass.

[73] Assignee: The DuPont Merck Pharmaceutical Company, Wilmington, Del.

[21] Appl. No.: 391,756

[22] Filed: Feb. 21, 1995

Related U.S. Application Data

[62] Division of Ser. No. 98,442, Aug. 3, 1993, Pat. No. 5,420,321.

[51] Int. Cl.$^6$ ............................. A61K 51/04; C07F 13/00
[52] U.S. Cl. ............................. 424/1.65; 534/10; 534/14
[58] Field of Search .................... 534/10, 14; 424/1.11, 424/1.65

[56] References Cited

U.S. PATENT DOCUMENTS

| | | | |
|---|---|---|---|
| 3,117,938 | 1/1964 | Burrus et al. | 252/429 |
| 4,452,774 | 6/1984 | Jones et al. | 424/1.1 |
| 4,707,544 | 11/1987 | Jones et al. | 534/14 |
| 4,735,793 | 4/1988 | Jones et al. | 424/1.1 |
| 4,826,961 | 5/1989 | Jones et al. | 534/14 |
| 4,872,561 | 10/1989 | Jones et al. | 206/569 |
| 4,885,100 | 12/1989 | Iqbal et al. | 252/1 |
| 4,894,445 | 1/1990 | Carpenter, Jr. et al. | 534/14 |
| 4,988,827 | 1/1991 | Bergstein et al. | 549/451 |
| 5,008,418 | 4/1991 | Iqbal et al. | 556/112 |
| 5,324,824 | 6/1994 | Carpenter, Jr. et al. | 534/14 |
| 5,346,995 | 9/1994 | Te-Wei et al. | 534/14 |
| 5,407,653 | 4/1995 | Piwnica-Worms | 424/1.11 |
| 5,420,321 | 5/1995 | Edwards | 536/112 |

OTHER PUBLICATIONS

Holman et al., *J. Nuc. Med.*, 25, p. 1380 (1984).
Kahn et al., *Circulation* 79, pp. 1282–1293 (1989).
Iskandrian et al., *Amer. J. Cardiol.* 64, pp. 270–275 (1989).
Christian et al., *Circulation* 83, pp. 1615–1620 (1991).

*Primary Examiner*—John Kight
*Assistant Examiner*—Lara C. Kelley
*Attorney, Agent, or Firm*—Gerald J. Boudreaux; David H. Vance

[57] ABSTRACT

Tris(isonitrile) copper(I) sulfate complexes and their use in synthetic methods for making radionuclide isonitrile coordination complexes such as [$^{99m}$Tc(1-isocyano-2-methoxy-2-methylpropane)$_6$]$^+$. The coordination complexes are useful as radiopharmaceutical imaging agents.

34 Claims, No Drawings

TRIS(ISONITRILE) COPPER(I) SULFATES FOR PREPARING RADIONUCLIDE COMPLEXES

This is a division of application Ser. No. 08/098,442, filed Aug. 3, 1993 now U.S. Pat. No. 5,420,321.

FIELD OF THE INVENTION

This invention relates to methods, compounds and formulations for preparing radiopharmaceutical imaging agents, in particular, Tc-99m isonitrile complexes.

BACKGROUND OF THE INVENTION

Isonitrile complexes of a number of radionuclides that are useful as radiopharmaceuticals are described by Jones et. al. in U.S. Pat. No. 4,452,774. The complexes are described as being useful for visualizing cardiac tissue, detecting the presence of thrombi in the lungs and other types of blood perfusion defects, studying lung function, studying renal excretion and imaging the bone marrow and the hepatobiliary system. In practice, however, these complexes containing simple hydrocarbon isonitrile ligands have moderately high uptake in the lungs and liver of humans. See, e.g., Holman et. al., *J. Nucl. Med.* 25, 1380 (1984). This uptake can interfere with the visualization of cardiac tissue.

The problem of lung and liver uptake can be partially overcome by using the isonitrile complexes described by Jones et. al. in U.S. Pat. Nos. 4,735,793 and 4,872,561. These ester or amide isonitrile complexes generally give better lung and liver clearance, thus allowing earlier or higher contrast imaging. A superior series of ether-substituted isonitrile complexes are described by Bergstein and Subramanyan in U.S. Pat. No. 4,988,827. These ether-substituted isonitrile complexes have been extensively evaluated in vivo. Clinical evaluations of technetium-99m (Tc-99m) ether-substituted isonitrile complexes are reported in Kahn et. al., *Circulation* 79, 1282–1293 (1989); Iskandriam et. al., *Amer. J. Cardiol.* 64, 270–275 (1989); and Christian et. al., *Circulation* 83, 1615–1620 (1991).

The development of a process for the commercial manufacture of lyophilized kits for the preparation of Tc-99m isonitrile complexes was complicated by the volatility of the isonitrile ligands. Carpenter, Jr. et. al. described in U.S. Pat. No. 4,894,445 a solution to this problem by the synthesis of isonitrile adducts of non-radioactive metals such as Cu, Mo, Pd, Co, Ni, Cr, Ag and Rh. The metal-isonitrile adducts are chosen so that when combined with a radioactive metal in an appropriate media, the metal will be displaced by the radioactive metal to form the desired radiopharmaceutical. The copper complexes described are bis(isonitrile) phenanthroline and tetrakis(isonitrile) complexes. Many such adducts react with the desired metal radionuclide (e.g., Tc-99m) at elevated temperature to produce the radiopharmaceutical relatively rapidly. However, the heating requirement is inconvenient and cumbersome in the hospital setting.

Iqbal et. al. describe in U.S. Pat. No. 4,885,100 tris(isonitrile)copper(I) adducts with an anion selected from $BF_4$, $PF_6$, $ClO_4$, I, Br, Cl and $CF_3COO$. These adducts react with radionuclides, such as Tc-99m, and provide more rapid preparation of radiopharmaceuticals at room temperature than the complexes described by Carpenter, Jr. et. al. However, the technology described by Iqbal et. al. does not give sufficiently high yields of Tc-99m-isonitrile complexes after sufficiently short time periods to be practical in a busy hospital setting.

Consequently, a need exists for facile, efficient and cost-effective reagents and methods for preparation of radionuclide complexes.

SUMMARY OF THE INVENTION

Accordingly, one aspect of the present invention is a tris(isonitrile)copper(I) sulfate complex which is useful for the rapid synthesis of radionuclide isonitrile complexes, in high yield, at about room temperature.

Another aspect of the invention is a method for preparing a tris(isonitrile)copper(I) sulfate complex comprising:

(a) reacting one equivalent of tetrakis(acetonitrile)copper (I) sulfate with six equivalents of an isonitrile ligand; and (b) isolating a solid tris(isonitrile)copper(I) sulfate complex.

A third aspect of the invention is a method for preparing a coordination complex of an isonitrile ligand and a radionuclide comprising reacting a copper(I) sulfate complex of the isonitrile ligand with the radionuclide in a solvent to replace the copper with the radionuclide, thereby forming the coordination complex.

A fourth aspect of the invention is a sterile, non-pyrogenic kit for preparing a complex of a radionuclide and an isonitrile ligand comprising the tris(isonitrile)copper(I) sulfate complex as described above, a transfer agent and a reducing agent capable of reducing a radionuclide in respective amounts sufficient to form the complex of the radionuclide and the isonitrile ligand.

DETAILED DESCRIPTION OF THE PREFERRED EMBODIMENTS

An aspect of the present invention is a tris(isonitrile) copper(I) sulfate complex which is useful for preparing radiopharmaceutical diagnostic imaging agents. In general, use of the tris(isonitrile)copper(I) sulfate complex for preparing imaging agents is more facile, efficient and provides higher yields than the prior art complexes.

The tris(isonitrile)copper(I) sulfate complex of the present invention can be prepared using any isonitrile ligand. Exemplary isonitrile ligands include those having the formula CNR where R is an organic radical of 1–30 carbon atoms which can be aliphatic or aromatic and can be substituted with a variety of groups which may or may not be charged. The aromatic R group can include phenyl, tolyl, xylyl, naphthyl and biphenyl, each optionally substituted with halo, hydroxy, nitro, alkyl of 1–15 carbon atoms, alkyl ether of 1–15 carbon atoms and alkyl ester of 1–15 carbon atoms. The aliphatic R group can include alkyl, preferably containing 1–20 carbon atoms, such as methyl, ethyl, n-propyl, isopropyl, n-butyl, t-butyl, isobutyl, n-hexyl, 2-ethylhexyl, dodecyl and stearyl, alkenyl, alkynyl or cycloalkyl, each optionally substituted with halo, hydroxy, nitro, alkyl of 1–10 carbon atoms, alkyl ether of 1–10 carbon atoms and alkyl ester of 1–10 carbon atoms. Specific examples of suitable isonitrile ligands can be found in U.S. Pat. Nos. 4,452,774, 4,735,793, 4,872,561 and 4,988,827, which are incorporated herein by reference.

A preferred tris(isonitrile)copper(I) sulfate salt of the invention is represented by the formula (I):

$$[Cu(CNR)_3]_2[SO_4] \qquad (I)$$

where R is alkyl of 1–20 carbon atoms or has the formula (II) or (IIA):

where A is a straight or branched chain alkyl group and $R^1$ and $R^2$ each independently is a straight or branched chain alkyl group or taken together are a straight or branched chain alkylene group, provided that:

(1) the total number of carbon atoms in A plus $R^1$ in formula (II) is 4 to 6, provided further that when the total number of carbon atoms is 6, then the carbon atom beta to the isonitrile group is a quaternary carbon, and (2) the total number of carbon atoms in A plus $R^1$ plus $R^2$ in formula (IIA) is 4 to 9.

A most preferred sulfate salt is where the isonitrile ligand is methoxyisobutylisonitrile (MIBI), i.e., where R is a methoxyisobutyl radical. This compound, tris(MIBI)copper(I) sulfate, also known by its IUPAC name, tris(1-isocyano-2-methoxy-2-methylpropane)copper(I) sulfate, is referred to hereinafter as $[Cu(MIBI)_3]_2[SO_4]$.

The tris(isonitrile)copper(I) sulfate complexes of the present invention are more water soluble than the tris (isonitrile)copper(I) adducts disclosed by Iqbal et al. in U.S. Pat. No. 4,885,100. The adducts of Iqbal et al. include an anion selected from $BF_4$, $PF_6$, $ClO_4$, I, Br, Cl and $CF_3COO$ and exist as cationic or neutral complexes having a maximum solubility in water of 2–3 mg/mL due to the limited water solubility of the anion or the absence of charge on the complex. In contrast, the sulfate complexes of the present invention exhibit water solubility in excess of 2–3 mg/mL and preferably in excess of 100 mg/mL, such as in the case of $[Cu(MIBI)_3]_2[SO_4]$.

Another aspect of the present invention is a method for preparing the tris(isonitrile)copper(I) sulfate complexes described above. The sulfate complexes can be synthesized by the exchange of acetonitrile molecules in tetrakis (acetonitrile)copper(I) sulfate, i.e., $[Cu(CH_3CN)_4]_2[SO_4]$, with isonitrile ligands of the formula CNR, where R is as defined above.

The $[Cu(CH_3CN)_4]_2[SO_4]$ can be prepared in situ by heating a mixture of copper(II) sulfate, an excess of one equivalent of copper powder and an excess of eight equivalents of acetonitrile. Addition of six equivalents of isonitrile ligand to one equivalent of $[Cu(CH_3CN)_4]_2[SO_4]$ in a suitable organic solvent such as acetone, acetonitrile, methylene chloride or chloroform at about 0° C. quantitatively yields $[Cu(CNR)_3]_2[SO_4]$. Equations 1 and 2 summarize the reaction steps.

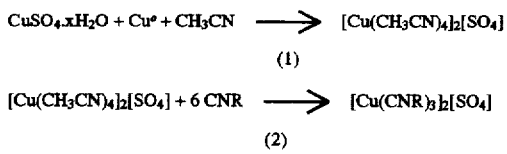

Crude tris(isonitrile)copper(I) sulfate complex product is isolated by filtration of the resulting solution, evaporation of the volatiles and precipitation from acetone by addition of diethyl ether. The product is then recrystallized successively from hot acetone.

Another aspect of the invention is a method for preparing isonitrile radionuclide coordination complexes. The radionuclide is a radioactive isotope of Tc, Ru, Co, Pt, Fe, Os, Ir, W, Re, Cr, Mo, Mn, Ni, Rh, Pd, Nb or Ta. Preferably, the radionuclide is Tc-99m. The radiolabelled isonitrile complexes are prepared by mixing a copper isonitrile complex with the radionuclide in a solvent to replace the copper with the radionuclide and form the coordination complex. Exemplary solvents include water, dimethyl sulfoxide, dimethyl formamide, methanol, ethanol, 1- or 2-propanol, acetone or acetonitrile. Preferably, the solvent is water or saline. The reaction temperatures can range from room temperature to reflux temperatures or even higher. Preferably, the reaction is carried out at about room temperature. The radiolabelled isonitrile complexes are isolable and are obtained in relatively high yields after relatively short reaction times.

In the case of technetium, Tc-99m isonitrile complexes are preferably made by mixing an amount of tris(isonitrile)copper(I) sulfate, an amount of a transfer agent and an amount of a reducing agent (capable of reducing pertechnetate ($^{99m}TcO_4^-$) in aqueous medium) in respective amounts sufficient to form the radiolabelled isonitrile complex. Any order of addition of the components can be used. Optionally, an amount of a cyclodextrin sufficient to facilitate the formation of the radiolabelled isonitrile complex can be added prior to the addition of the pertechnetate. Also optionally, a pharmaceutically acceptable buffering agent, such as citrate or phosphate, or a lyophilization aid, such as maltol or maltose, or both, may be added. Preferably, the amount of the tris(isonitrile)copper(I) sulfate is about 0.1 mg to about 100 mg, the amount of the transfer agent is about 0.05 mg to about 5 mg, the amount of the reducing agent is about 5 µg to about 5 mg, the amount of the optional cyclodextrin is about 1 mg to about 100 mg, the amount of the optional buffering agent is about 0.1 mg to 25 mg, and the amount of the optional lyophilization aid is 1 weight percent to 10 weight percent.

Preferably, the transfer agent is cysteine hydrochloride or a salt thereof. Alkyl esters of cysteine such as cysteine methyl ester (CME) and cysteine ethyl ester (CEE) are also preferred. CME is most preferred.

Certain of the isonitrile ligands useful in the invention can act as a reducing agent, eliminating the need for an additional reducing agent. Additional reducing agents are used when required or desired to increase the reaction rate. Exemplary reducing agents are stannous salts such as stannous chloride dihydrate, formamidine sulfinic acid, sodium dithionite, sodium bisulfite, hydroxylamine, ascorbic acid and the like.

An exemplary cyclodextrin which may also be included in the labeling reaction is gamma-cyclodextrin. Cyclodextrins are believed to function by providing preorganization of reactants in their hydrophobic cavities or pockets thus enhancing the rate of the reaction.

The reaction is generally complete after about 1 minute to about 2 hours, depending upon the particular reagents employed and the conditions used. Yields of radionuclide isonitrile coordination complexes prepared by the method of the invention range from about 71% to about 85% after about 15 minutes reaction time at about 26° C. to about 87% to about 95% after 35 minutes reaction time at about 26° C. The yields obtained at 15 minutes exceed the best obtained in 30 minutes using the technology disclosed in U.S. Pat. No. 4,885,100 of Iqbal et al.

For example, when the appropriate amounts of [Cu(MIBI)$_3$]$_2$[SO$_4$], cysteine hydrochloride (as transfer agent) and the reducing agent stannous chloride dihydrate are reacted with $^{99m}TcO_4^-$ at room temperature, yields of $^{99m}Tc(MIBI)_6^+$ ranging from about 71 to about 76% at 15 minutes and reaching about 87% at 35 minutes are obtained.

When an ester of cysteine is used as the transfer agent, even higher yields of Tc-99m isonitrile complexes are obtained. For example, the reaction of appropriate amounts of [Cu(MIBI)$_3$]$_2$[SO$_4$], cysteine ethyl ester hydrochloride and stannous chloride dihydrate with $^{99m}$TcO$_4^-$ at room temperature, results in about 74% yield of $^{99m}$Tc(MIBI)$_6^+$ at 15 minutes and about 90% at 35 minutes. The reaction of appropriate amounts of [Cu(MIBI)$_3$]$_2$[SO$_4$], cysteine methyl ester hydrochloride and stannous chloride dihydrate with $^{99m}$TcO$_4^-$ at room temperature, results in about 85% yield of $^{99m}$Tc(MIBI)$_6^+$ at 15 minutes and about 91% at 35 minutes. When gamma-cyclodextrin is included in a mixture of appropriate amounts of [Cu(MIBI)$_3$]$_2$[SO$_4$], cysteine methyl ester hydrochloride and stannous chloride dihydrate, the reaction with $^{99m}$TcO$_4^-$ at room temperature results in about 78% yield of $^{99m}$Tc(MIBI)$_6^+$ at 15 minutes and about 95% at 35 minutes.

Kits for preparing a complex of a radionuclide and an isonitrile ligand in accord with the present invention are sterile and non-pyrogenic and comprise a tris(isonitrile) copper(I) sulfate complex, a transfer agent and a reducing agent for reducing a radionuclide in respective amounts sufficient to form the complex of the radionuclide and the isonitrile ligand. Optionally, the kits may contain a cyclodextrin, a buffering agent, a lyophilization aid, or any combination thereof. Preferably, such kits contain about 0.1 to about 100 mg of the tris isonitrile copper(I) sulfate complex, about 0.05 to about 5 mg of the transfer agent, about 0.005 to about 5000 mg of the reducing agent and optionally about 1 to about 100 mg of a cyclodextrin, 0.1 to 25 mg of a buffering agent, or 1 to 10 weight percent of a lyophilization aid. It is also preferable that the contents of the kits be lyophilized, if possible, to facilitate storage. If lyophilization is not possible, the kits can be stored frozen. The components are preferably contained in sealed, non-pyrogenic, sterilized containers.

The present invention will now be described in more detail with reference to the following specific, non-limiting examples.

EXAMPLES

Analytical Methods

High pressure liquid chromatography (HPLC) and thin layer chromatography (TLC) were used to determine the radiochemical purity (RCP) of Tc-99m labelled product. Radiochemical purity reflects percent yield of the radionuclide isonitrile complex.

Aliquots of the labelling reaction mixtures described below were chromatographed on Whatman C18 reverse-phase thin layer chromatographic plates developed with a 40% acetonitrile, 30% methanol, 20% 0.5M ammonium acetate and 10% tetrahydrofuran solvent system. The 99mTc labelling species produced from the pertechnetate and radionuclide isonitrile complex are separated in this system from colloidal material which is formed as a byproduct of the labelling reaction. Radioanalytical HPLC was performed on μBondapak C$_{18}$ (4.6 mm×250 mm) column (Waters Associates). The column was eluted at a flow rate of 1.5 mL/min with a linear gradient of 100% solvent A (700:300:1 water:acetonitrile:trifluoroacetic acid) to 100% solvent B (100:900:1 water:acetonitrile:trifluoroacetic acid) over 10 minutes, held at 100% solvent B for one minute and then returned to 100% solvent A. The RCP, colloid and corrected RCP data in the following Examples are reported in percent. Corrected RCP data were determined from the average of two RCP values from HPLC corrected for the average of three colloid values as determined by TLC, i.e., where % corrected RCP=[(100-% colloid(by TLC))/100](% RCP (by HPLC)).

Example 1

Multivariant Parametric Analysis of the Technology Described in U.S. Pat. No. 4,885,100

Empirical evidence has indicated that the technology described by Iqbal et. al. in U.S. Pat. No. 4,885,100 does not give sufficiently high yields of Tc-99m isonitrile complexes after sufficiently short time periods to be practical in a busy hospital setting. Based on an extensive multivariant parametric analysis, it has been determined that the Iqbal et al. technology provides maximum yields of the Tc-99m isonitrile complex, [$^{99m}$Tc(MIBI)$_6$]$^+$, of only 30% and 68% at 10 minute and 30 minute time points, respectively.

The study was statistically designed using a commercially available software package RSDiscover (Bolt Beranek & Newman, Cambridge, Mass.). A five-factor, 32 experiment, Face Centered Cubic design was used. The factors included the [Cu(MIBI)$_3$][BF$_4$] level, stannous chloride dihydrate level, cysteine hydrochloride hydrate level, mannitol level and the pH and are listed in Table 1. The sodium citrate dihydrate buffer component was fixed. The three levels chosen for each factor were: [Cu(MIBI)$_3$][BF$_4$] 0.5, 1.25 and 2.0 mg/vial; stannous chloride 10, 105 and 200 μg/vial; cysteine 3, 7.5 and 12 mg/vial; mannitol 5, 15 and 25 mg/vial and pH 3, 4.5 and 6. The required amounts of the components mannitol, cysteine hydrochloride hydrate, [Cu(MIBI)$_3$][BF$_4$], stannous chloride dihydrate as indicated in Table 1 and a constant amount of sodium citrate dihydrate were dissolved in a 10.0 mL volumetric flask using argon-sparged, deionized water, adjusting the pH, and diluting to the mark. 1.0 mL of the resulting solution was dispensed into each of three vials that were then placed in a temperature controlled water bath at 26° C. 1.0 mL of Na$^{99m}$TcO$_4^-$ solution (50 mCi/mL obtained from a $^{99}$Mo/$^{99m}$TC radionuclide generator) prepared in 1.8 wt. % saline was added to each vial. The yield of the product [$^{99m}$Tc(MIBI)$_6$]$^+$ at 10 and 30 minutes was determined by the TLC and HPLC methods described above. Two vials were analyzed by both TLC and HPLC, while the third vial was analyzed by TLC only. The data are reported in Table 2.

TABLE 1

Component Levels for Response Surface Study

| Run | Mannitol (mg) | Cysteine (mg) | [Cu(MIBI)$_3$][BF$_4$](mg) | Stannous (μg) | pH |
|---|---|---|---|---|---|
| 1 | 25.77 | 11.5 | 1.95 | 200 | 6.17 |
| 2 | 15.05 | 7.77 | 1.26 | 105 | 4.37 |
| 3 | 25.60 | 2.94 | 0.51 | 10 | 3.22 |
| 4 | 4.96 | 3.07 | 0.50 | 200 | 3.20 |
| 5 | 14.95 | 2.85 | 1.28 | 105 | 4.33 |
| 6 | 5.07 | 7.90 | 1.30 | 105 | 4.37 |
| 7 | 14.82 | 7.56 | 1.29 | 200 | 4.41 |
| 8 | 24.93 | 12.16 | 0.47 | 200 | 3.01 |
| 9 | 4.88 | 12.07 | 199 | 200 | 2.82 |
| 10 | 4.96 | 11.96 | 0.49 | 200 | 6.25 |
| 11 | 14.82 | 7.56 | 1.93 | 105 | 4.44 |
| 12 | 25.00 | 7.69 | 1.30 | 105 | 4.50 |
| 13 | 24.90 | 12.00 | 0.51 | 10 | 6.10 |
| 14 | 15.00 | 7.40 | 1.30 | 105 | 4.57 |
| 15 | 4.91 | 2.98 | 1.95 | 200 | 6.12 |
| 16 | 5.19 | 3.01 | 1.97 | 10 | 2.98 |
| 17 | 5.11 | 12.06 | 1.95 | 10 | 5.90 |
| 18 | 14.98 | 7.57 | 1.28 | 10 | 4.62 |
| 19 | 14.98 | 7.43 | 1.31 | 105 | 3.16 |
| 20 | 25.03 | 12.12 | 2.01 | 10 | 3.17 |
| 21 | 15.14 | 7.47 | 1.27 | 105 | 4.46 |
| 22 | 25.31 | 3.06 | 2.01 | 200 | 3.01 |
| 23 | 15.06 | 7.49 | 1.26 | 105 | 4.44 |
| 24 | 25.14 | 2.95 | 0.55 | 200 | 5.97 |

TABLE 1-continued

Component Levels for Response Surface Study

| Run | Mannitol (mg) | Cysteine (mg) | [Cu(MIBI)₃][BF₄](mg) | Stannous (μg) | pH |
|---|---|---|---|---|---|
| 25 | 15.00 | 7.50 | 1.30 | 105 | 4.43 |
| 26 | 15.30 | 7.40 | 0.60 | 105 | 4.43 |
| 27 | 24.90 | 3.00 | 2.00 | 10 | 5.97 |
| 28 | 4.93 | 2.9 | 0.50 | 10 | 5.96 |
| 29 | 15.03 | 12.08 | 1.24 | 105 | 4.63 |
| 30 | 14.91 | 7.41 | 1.35 | 105 | 4.61 |
| 31 | 5.00 | 12.03 | 0.53 | 10 | 3.12 |
| 32 | 14.89 | 7.41 | 1.31 | 105 | 6.07 |

TABLE 2

Response Surface Study Data

| | Colloid (avg.) | | RCP (avg.) | | Corrected RCP | |
|---|---|---|---|---|---|---|
| Run # | t = 10 min | t = 30 min | t = 10 min | t = 30 min | t = 10 min | t = 30 min |
| 1 | 2.29 | 1.92 | 18.16 | 51.08 | 17.74 | 50.10 |
| 2 | 14.14 | 17.12 | 25.74 | 45.07 | 22.10 | 37.35 |
| 3 | 16.29 | 10.24 | 7.66 | 17.67 | 6.41 | 15.86 |
| 4 | 30.53 | 42.31 | 7.80 | 12.62 | 5.42 | 7.28 |
| 5 | 11.73 | 21.08 | 29.62 | 50.74 | 26.15 | 40.04 |
| 6 | 10.88 | 18.52 | 25.62 | 47.49 | 22.83 | 38.69 |
| 7 | 14.58 | 22.76 | 25.60 | 51.32 | 21.87 | 39.64 |
| 8 | 29.49 | 41.81 | 17.44 | 34.93 | 12.30 | 20.33 |
| 9 | 22.46 | 33.65 | 31.42 | 60.12 | 24.36 | 39.89 |
| 10 | 12.22 | 21.48 | 9.03 | 37.15 | 7.93 | 29.17 |
| 11 | 8.13 | 10.61 | 28.90 | 48.04 | 26.55 | 42.94 |
| 12 | 9.37 | 13.27 | 25.16 | 48.55 | 22.80 | 42.11 |
| 13 | 0.0 | 0.0 | 0.0 | 0.0 | 0.0 | 0.0 |
| 14 | 10.61 | 14.53 | 26.06 | 51.41 | 23.30 | 43.94 |
| 15 | 4.88 | 4.65 | 32.14 | 70.32 | 30.57 | 67.05 |
| 16 | 6.86 | 9.85 | 28.70 | 46.96 | 26.73 | 42.33 |
| 17 | 0.0 | 0.0 | 0.0 | 0.0 | 0.0 | 0.0 |
| 18 | 3.13 | 2.21 | 28.42 | 55.04 | 27.53 | 53.82 |
| 19 | 19.16 | 34.81 | 23.87 | 42.58 | 19.30 | 27.76 |
| 20 | 6.28 | 4.84 | 31.00 | 58.15 | 29.05 | 55.34 |
| 21 | 13.07 | 11.93 | 42.01 | 57.37 | 36.52 | 50.53 |
| 22 | 36.65 | 45.23 | 38.02 | 55.22 | 24.09 | 30.24 |
| 23 | 15.23 | 18.46 | 26.57 | 46.80 | 22.52 | 38.16 |
| 24 | 13.24 | 15.01 | 25.71 | 62.94 | 22.31 | 53.49 |
| 25 | 9.56 | 15.16 | 24.80 | 47.81 | 22.43 | 40.56 |
| 26 | 15.38 | 25.54 | 20.48 | 39.17 | 17.33 | 29.17 |
| 27 | 0.0 | 0.0 | 0.37 | 0.31 | 0.37 | 0.31 |
| 28 | 0.35 | 1.37 | 23.49 | 55.48 | 23.41 | 54.72 |
| 29 | 8.78 | 13.29 | 24.71 | 55.19 | 22.54 | 47.86 |
| 30 | 9.57 | 14.24 | 31.29 | 53.52 | 28.30 | 45.90 |
| 31 | 7.20 | 7.04 | 17.95 | 37.29 | 16.66 | 34.66 |
| 32 | 2.55 | 2.20 | 25.71 | 55.02 | 25.05 | 53.81 |

The corrected % RCP of [⁹⁹ᵐTc(MIBI)₆]⁺ data were entered as responses in the experimental design. The data were then modeled in RSDiscover. The Analysis of Variance (ANOVA) tables for the resulting models of the 10 minute [⁹⁹ᵐTc(MIBI)₆]⁺ yield (Table 3) and the 30 minute [⁹⁹ᵐTc(MIBI)₆]⁺ yield (Table 4) are shown below. In Tables 3 and 4, M=mannitol, CY=cysteine, MI=[Cu(MIBI)₃][BF₄], T=SnCl₂.2H₂O, and p=pH.

TABLE 3

Least Squares Components ANOVA for RCP at 10 minutes

| Source | deg. freedom | Sum sq. | Mean sq. | F-ratio | Signif. |
|---|---|---|---|---|---|
| Constant | 1 | 12579.756 | — | — | — |
| M | 1 | 11.203 | 11.203 | 0.53 | 0.4754 |
| CY | 1 | 61.130 | 61.130 | 2.89 | 0.1053 |
| MI | 1 | 276.770 | 276.770 | 13.10 | 0.0018 |
| T | 1 | 71.992 | 71.992 | 3.41 | 0.0806 |
| P | 1 | 96.000 | 96.000 | 4.54 | 0.0463 |
| M*CY | 1 | 144.581 | 144.581 | 6.84 | 0.0170 |
| M*T | 1 | 88.552 | 88.552 | 4.19 | 0.0547 |
| CY*P | 1 | 351.481 | 351.481 | 16.63 | 0.0006 |
| MI**2 | 1 | 563.046 | 563.046 | 26.65 | 0.0001 |
| MI*T | 1 | 86.777 | 86.777 | 4.11 | 0.0570 |
| MI*P | 1 | 312.008 | 312.008 | 14.77 | 0.0011 |
| T*P | 1 | 291.250 | 291.250 | 13.78 | 0.0015 |
| Residual | 19 | 401.465 | 21.130 | — | — |

Root mean square error=0.8491
Root mean square error adjusted=0.7538

TABLE 4

Least Squares Components ANOVA for RCP at 30 minutes

| Source | deg. freedom | Sum sq. | Mean sq. | F-ratio | Signif. |
|---|---|---|---|---|---|
| Constant | 1 | 43001.447 | — | — | — |
| M | 1 | 49.237 | 49.237 | 0.80 | 0.3827 |
| CY | 1 | 56.214 | 56.214 | 0.91 | 0.3517 |
| MI | 1 | 432.923 | 432.923 | 7.04 | 0.0162 |
| T | 1 | 352.968 | 352.968 | 5.74 | 0.0277 |
| P | 1 | 66.529 | 66.529 | 1.08 | 0.3121 |
| M*CY | 1 | 605.900 | 605.900 | 9.85 | 0.0057 |
| M*T | 1 | 324.563 | 324.563 | 5.28 | 0.0338 |
| CY*MI | 1 | 142.077 | 142.077 | 2.31 | 0.1459 |
| CY*P | 1 | 1640.296 | 1640.296 | 26.67 | 0.0001 |
| MI**2 | 1 | 993.176 | 993.176 | 16.15 | 0.0008 |
| MI*T | 1 | 424.118 | 424.118 | 6.90 | 0.0171 |
| MI*P | 1 | 846.989 | 846.989 | 13.77 | 0.0016 |
| T*P | 1 | 2380.371 | 2380.371 | 38.71 | 0.0000 |
| Residual | 18 | 1106.913 | 61.495 | — | — |

Root mean square error=0.8780
Root mean square error adjusted=0.7898

The ANOVA tables show that a model can be generated for the 10 minute [⁹⁹ᵐTc(MIBI)₆]⁺ yield data that explains 75% of the variability in the data. A similar model can be generated for the 30 minute [⁹⁹ᵐTc(MIBI)₆]⁺ yield data that explains 79% of the variability.

Using these models, the predicted maximum yield of [⁹⁹ᵐTc(MIBI)₆]⁺ using the methodology and reagents disclosed by Iqbal et al. in U.S. Pat. No. 4,885,100 is 31% at 10 minutes and 75% at 30 minutes. The values of the 5 factors at the predicted maximum were [Cu(MIBI)₃][BF₄] =1.9 mg, SnCl₂.2H₂O=192 μg, pH=6, mannitol=5 mg and cysteine=3 mg. When this formulation was tested, a 30% yield at 10 minutes and a 68% yield at 30 minutes were obtained. The observed yields were slightly lower than the predicted yields, but well within the standard deviations of the predicted values.

Example 2

Synthesis of [Cu(MIBI)₃]₂[SO₄].0.5 acetone

CuSO₄.5H₂O (24.5 g, 98.1 mmol) and copper metal (12.6 g, 198 mmol) were placed in a 500 mL Schlenk flask under a nitrogen atmosphere followed by 200 mL nitrogen-sparged acetone and 75 mL nitrogen-sparged acetonitrile. The reaction mixture was refluxed under nitrogen for 1.5 hours and then cooled in an ice bath. A large amount of white crystalline solids formed. 2-methoxyisobutylisonitrile (MIBI) (66.6 g, 588 mmol) was then added dropwise over 2 hours. The reaction mixture was allowed to warm to room temperature and stirred for 12 hours. The excess copper metal was filtered off using Schlenk techniques and the volatiles evaporated from the green-colored filtrate. The yellow-green syrupy residue was dissolved in a minimal amount (~200 mL) of acetone (distilled from $B_2O_3$, degassed) and then 400 mL of anhydrous diethyl ether was added dropwise with vigorous stirring. An off-white oily solid precipitated and was isolated on a medium Schlenk filter then dried under vacuum. The crude product was recrystallized three times from a minimal amount of hot acetone in an argon glovebox yielding a white crystalline solid (15.0 g, 16.1 mmol). $^1$H NMR (CDCl$_3$, 270 MHz) spectral data were as follows: 3.58 (s, 12 H, CH$_2$), 3.20 (s, 18 H, OCH$_3$), 2.12 (s, 3 H, acetone), 1.24 (s, 36 H, CH$_3$). Calculated elemental analysis for $C_{37.5}H_{69}N_6O_{10.5}SCu_2$ was: %C, 48.37; %H, 7.47; %N, 9.03; %Cu, 13.65.; found was: %C, 48.56; %H, 7.43; %N, 8.79; %Cu, 13.4.

Examples 3–5

Effect of Tris(isonitrile)copper(I) Sulfate and Transfer Agent on Yield of [$^{99m}$Tc(MIBI)$_6$]$^+$ Amounts of [Cu(MIBI)$_3$]$_2$[SO$_4$].0.5 acetone and cysteine hydrochloride hydrate as indicated in Table 5 were dissolved together with 0.27 mmol of mannitol, 0.17 mmol sodium citrate dihydrate and 0.009 mmol stannous chloride dihydrate in a 10.0 mL volumetric flask using argon-sparged, deionized water, adjusting the pH and diluting to the mark. 1.0 mL of the resulting solution was dispensed into each of three vials that were then placed in a temperature controlled water bath at 26° C. 1.0 mL of Na$^{99m}$TcO$_4$ (50 mCi/mL) solution prepared as in Example 1 was added to each vial and the corrected % RCP determined at 15 and either 35 or 40 minutes. The data are reported in Table 5.

TABLE 5

Effect of [Cu(MIBI)$_3$]$_2$[SO$_4$] Level and Cysteine Level on [$^{99m}$Tc(MIBI)$_6$]$^+$ Yield

| Example No. | Cys (mmol) | MIBI* (mmol) | pH | Colloid t = 15 min | Colloid t = 35 min | RCP corr. t = 15 | RCP corr. t = 35 |
|---|---|---|---|---|---|---|---|
| 3 | 0.008 | 0.067 | 5.8 | 3.3 | n.d. | 71 | n.d. |
| 4 | 0.008 | 0.200 | 5.8 | 2.2 | n.d. | 74 | n.d. |
| 5 | 0.016 | 0.067 | 5.2 | 4.6 | 4.0 | 76 | 87 |

*MIBI refers to molar concentration of MIBI in the form of [Cu(MIBI)$_3$]$_2$[SO$_4$], calculated by [Cu salt] × 6.

The results show the effect of using higher concentrations of [Cu(MIBI)$_3$]$^+$, attainable by using the more soluble sulfate salt [Cu(MIBI)$_3$]$_2$[SO$_4$]. The 15 minute yields of [$^{99m}$Tc(MIBI)$_6$]$^+$ are significantly increased over those obtained using the technology disclosed in Iqbal et al. U.S. Pat. No. 4,885,100. In fact, the 15 minute yield surpass those obtained at 30 minutes using the prior technology. There is also a beneficial effect on the yield by increasing the cysteine level, so that an 87% yield of [$^{99m}$Tc(MIBI)$_6$]$^+$ can be obtained after a 35 minute incubation under the conditions of Example No. 5.

Examples 6 and 7

Effect of Cysteine Alkyl Esters on [$^{99m}$Tc(MIBI)$_6$]$^+$ Yield

Amounts of [Cu(MIBI)$_3$]$_2$[SO$_4$].0.5 acetone and either cysteine methyl ester hydrochloride (CME) or cysteine ethyl ester hydrochloride (CEE) as indicated in Table 6 were dissolved together with 0.27 mmol of mannitol, 0.17 mmol sodium citrate dihydrate and 0.009 mmol stannous chloride dihydrate in a 10.0 mL volumetric flask using argon-sparged, deionized water, adjusting the pH and diluting to the mark. 1.0 mL of the resulting solution was dispensed into each of three vials that were then placed in a temperature controlled water bath at 26° C. 1.0 mL of Na$^{99m}$TcO$_4$ (50 mCi/mL) solution prepared as in Example 1 was added to each vial and the reactions monitored at 15 and 35 minutes. The data are presented in Table 6.

TABLE 6

Effect of Cysteine Alkyl Esters as Transfer Agents on [$^{99m}$Tc(MIBI)$_6$]$^+$ Yield

| Ex. No. | Transfer Agent | TA mmol | MIBI* mmol | pH | Colloid t = 15m | Colloid t = 35m | RCP corr. t = 15m | RCP corr. t = 35m |
|---|---|---|---|---|---|---|---|---|
| 6 | CME | 0.016 | 0.067 | 5.6 | 0 | 0 | 85 | 91 |
| 7 | CEE | 0.016 | 0.067 | 5.6 | 0.8 | 0.6 | 74 | 90 |

*MIBI refers to molar concentration of MIBI in the form of [Cu(MIBI)$_3$]$_2$[SO$_4$], calculated by [Cu salt] × 6.

The results demonstrate the beneficial effect of substituting alkyl esters of cysteine for cysteine as the transfer agent. The improvement in yield is mostly due to a significant lessening of the amount of $^{99m}$Tc colloid by-product formed. Yields as high as 85% can be obtained at 15 minutes using the preferred cysteine methyl ester as the transfer agent (Example No.7). The 35 minute yields in both Example Nos. 6 and 7 are ≧90%.

Example 8

Effect of Cyclodextrin on [$^{99m}$Tc(MIBI)$_6$]$^+$ Yield 0.011 mmol [Cu(MIBI)$_3$]$_2$[SO$_4$].0.5 acetone, 0.022 mmol cysteine methyl ester hydrochloride, 0.38 mmol gamma-cyclodextrin, 0.008 mmol sodium citrate dihydrate, 0.008 mmol anhydrous chromium(II) chloride and 0.0009 mmol stannous chloride dihydrate were dissolved in a 10.0 mL volumetric flask using argon-sparged, deionized water, adjusting the pH, and diluting to the mark. 1.0 mL of the resulting solution was dispensed into each of three vials that were then placed in a temperature controlled water bath (26° C). 1.0 mL of Na$^{99m}$TcO$_4^-$ (50 mCi/mL) solution prepared as in Example 1 was added to each vial and the reactions monitored at 15 and 35 minutes. The data are presented in Table 7.

TABLE 7

Effect of gamma-cyclodextrin on [] Yield

| Ex. No. | gamma-cyclodextrin mmol | CME mmol | MIBI* mmol | pH | Colloid t = 15m | Colloid t = 35m | RCP corr. t = 15m | RCP corr. t = 35m |
|---|---|---|---|---|---|---|---|---|
| 8 | 0.038 | 0.002 | 0.006 | 6.4 | 0.7 | 0.8 | 78 | 95 |

*MIBI refers to molar concentration of MIBI in the form of [Cu(MIBI)$_3$]$_2$[SO$_4$], calculated by [Cu salt] × 6.

These data demonstrate the beneficial effect of adding gamma-cyclodextrin to the reaction mixture. A yield of 78% is obtained at 15 minutes and 95% at 35 minutes while using significantly less [Cu(MIBI)$_3$]$_2$[SO$_4$] (0.001 vs. 0.01 mmol) and significantly less cysteine methyl ester (0.002 vs. 0.016 mmol) under these reaction conditions. This effect is due to the impact of preorganization of the reactants on the reaction rate.

The present invention may be embodied in other specific forms without departing from the spirit or essential attributes thereof and, accordingly, reference should be made to the appended claims, rather than to the foregoing specification, as indicating the scope of the invention.

I claim:

1. A method for preparing a coordination complex of an isonitrile ligand and a radionuclide comprising mixing a copper (I) sulfate complex of the isonitrile ligand with the radionuclide in a solvent to replace the copper with the radionuclide, thereby forming the coordination complex, wherein the radionuclide is a radioactive isotope of Tc, Ru, Co, Pt, Fe, Os, Ir, W, Re, Cr, Mo, Mn, Ni, Rh, Pd, Nb or Ta.

2. The method of claim 1 wherein the radionuclide is a radioactive isotope of Tc, Ru, Co, Pt, Fe, Os, Ir, W, Re, Cr, Mo, Mn, Ni, Rh, Pd, Nb or Ta.

3. The method of claim 1 wherein the radionuclide is a radioactive isotope of Tc.

4. The method of claim 3 wherein the radionuclide is Tc-99m.

5. The method of claim 1 wherein the isonitrile ligand has the formula CNR, where R is selected from: an aromatic ring system selected from the group: phenyl, tolyl, xylyl, naphthyl and biphenyl, each optionally substituted with halo, hydroxy, nitro, alkyl of 1–15 carbon atoms, alkyl ether of 1–15 carbon atoms and alkyl ester of 1–15 carbon atoms and an aliphatic group containing 1–20 carbon atoms selected from the group: methyl, ethyl, n-propyl, isopropyl, n-butyl, t-butyl, isobutyl, n-hexyl, 2-ethylhexyl, dodecyl, stearyl, alkenyl, alkynyl, and cycloalkyl, each optionally substituted with halo, hydroxy, nitro, alkyl of 1–10 carbon atoms, alkyl ether of 1–10 carbon atoms and alkyl ester of 1–10 carbon atoms.

6. The method of claim 5 wherein R is alkyl selected from the group of 1–20 carbon atoms or aryl of phenyl, tolyl, xylyl, naphthyl or biphenyl.

7. The method of claim 1 wherein the copper(I) sulfate complex of the isonitrile ligand has the formula (I):

[Cu(CNR)$_3$]$_2$[SO$_4$]     (I)

where R is alkyl of 1–20 carbon atoms or has the formula (II) or (IIA):

     (II)

or

     (IIA)

where A is a straight or branched chain alkyl group and R$^1$ and R$^2$ each independently is a straight or branched chain alkyl group or taken together are a straight or branched chain alkylene group, provided that:

(1) the total number of carbon atoms in A plus R$^1$ in formula (II) is 4 to 6, provided further that when the total number of carbon atoms is 6, then the carbon atom beta to the isonitrile group is a quaternary carbon, and (2) the total number of carbon atoms in A plus R$^1$ plus R$^2$ in formula (IIA) is 4 to 9.

8. The method of claim 7 wherein the solubility of the complex in water is in excess of 3 mg/mL.

9. The method of claim 8 wherein the solubility of the complex in water is in excess of 100 mg/ml.

10. The method of claim 7 wherein the copper(I) sulfate complex of the isonitrile ligand is tris(1-isocyano-2-methoxy-2-methylpropane)copper(I) sulfate.

11. The method of claim 1 further comprising including a transfer agent in the reaction.

12. The method of claim 11 wherein the transfer agent is cysteine or a salt thereof.

13. The method of claim 12 wherein the transfer agent is an alkyl ester of cysteine.

14. The method of claim 13 wherein the transfer agent is cysteine methyl ester.

15. The method of claim 13 wherein the transfer agent is cysteine ethyl ester.

16. The method of claim 1 further comprising including a reducing agent in the reaction.

17. The method of claim 16 wherein the reducing agent is a stannous salt, formamidine sulfinic acid, sodium dithionite, sodium bisulfite, hydroxylamine or ascorbic acid.

18. The method of claim 17 wherein the stannous salt is stannous chloride dihydrate.

19. The method of claim 1 further comprising including a cyclodextrin in the reaction.

20. The method of claim 19 wherein the cyclodextrin is gamma-cyclodextrin.

21. The method of claim 1 wherein the copper(I) sulfate complex of the isonitrile ligand and the radionuclide are mixed in water or saline at about room temperature.

22. The method of claim 1 wherein the radionuclide isonitrile coordination complex is formed in a yield of about 71% to about 95%.

23. A sterile, non-pyrogenic kit for preparing a complex of a radionuclide and an isonitrile ligand comprising a tris (isonitrile) copper (I) sulfate complex, a transfer agent and a reducing agent capable of reducing a radionuclide in respective amounts sufficient to form the complex of the radionuclide and the isonitrile ligand, wherein the radionuclide is a radioactive isotope of Tc, Ru, Co, Pt, Fe, Os, Ir, W, Re, Cr, Mo, Mn, Ni, Rh, Pd, Nb or Ta.

24. The kit of claim 23 wherein the amount of the tris(isonitrile)copper(I) sulfate complex is about 0.1 to about 100 mg, the amount of the transfer agent is about 0.05 to about 5 mg and the amount of the reducing agent is about 0.005 to about 5000 mg.

25. The kit of claim 23 wherein the components are lyophilized or frozen and the radionuclide is Tc-99m.

26. The kit of claim 23 wherein the transfer agent is cysteine or a salt thereof.

27. The kit of claim 26 wherein the transfer agent is an alkyl ester of cysteine.

28. The kit of claim 27 wherein the cysteine alkyl ester is cysteine methyl ester.

29. The kit of claim 27 wherein the cysteine alkyl ester is cysteine ethyl ester.

30. The kit of claim 23 wherein the reducing agent is stannous chloride dihydrate.

31. The kit of claim 23 further comprising a cyclodextrin in an amount sufficient to facilitate the formation of the complex of the radionuclide and the isonitrile ligand.

32. The kit of claim 31 wherein the cyclodextrin is gamma-cyclodextrin.

33. The kit of claim 32 wherein the amount of the gamma-cyclodextrin is about 1 to about 100 mg.

34. A kit according to claim 23, wherein the isonitrile ligand of the tris(isonitrile)copper (I) sulfate complex has the formula CNR, where R is selected from: an aromatic ring system selected from the group: phenyl, tolyl, xylyl, naphthyl and biphenyl, each optionally substituted with halo, hydroxy, nitro, alkyl of 1–15 carbon atoms, alkyl ether of 1–15 carbon atoms and alkyl ester of 1–15 carbon atoms and an aliphatic group containing 1–20 carbon atoms, methyl, ethyl, n-propyl, isopropyl, n-butyl, t-butyl, isobutyl, n-hexyl, 2-ethylhexyl, dodecyl, stearyl, alkenyl, alkynyl, and cycloalkyl, each optionally substituted with halo, hydroxy, nitro, alkyl of 1–10 carbon atoms, alkyl ether of 1–10 carbon atoms and alkyl ester of 1–10 carbon atoms.

* * * * *